United States Patent [19]
Liang et al.

[11] Patent Number: 6,048,990
[45] Date of Patent: *Apr. 11, 2000

[54] METHOD FOR SELECTIVE ACYLATION OF C-2'-O-PROTECTED-10-HYDROXY-TAXOL AT THE C-10 POSITION

[75] Inventors: Xian Liang; Jan Zygmunt, both of Boulder, Colo.; Nicholas J. Sisti, Mineola, N.Y.; Madhavi C. Chander, Boulder, Colo.; Herbert R. Brinkman, Superior, Colo.; James D. McChesney, Boulder, Colo.

[73] Assignee: NaPro BioTherapeutics, Inc., Boulder, Colo.

[ * ] Notice: This patent is subject to a terminal disclaimer.

[21] Appl. No.: 09/071,258

[22] Filed: May 1, 1998

[51] Int. Cl.[7] .................................................. C07D 305/14
[52] U.S. Cl. .......................................... 549/510; 549/511
[58] Field of Search ...................................... 549/510, 511

[56] References Cited

U.S. PATENT DOCUMENTS

| | | | |
|---|---|---|---|
| 4,924,011 | 5/1990 | Denis et al. | 549/510 |
| 4,924,012 | 5/1990 | Colin et al. | 549/510 |
| 5,015,744 | 5/1991 | Holton | 549/510 |
| 5,229,526 | 7/1993 | Holton | 549/213 |
| 5,675,025 | 10/1997 | Sisti et al. | 549/510 |
| 5,688,977 | 11/1997 | Sisti | 549/510 |

OTHER PUBLICATIONS

"A Chemoselective Approach to Functoinalize the C–10 Position of 10–Deacetylbaccatin III Synthesis and Biological Properties of Novel C–10 Taxol Analogues", by Kant et al, *Tetrahedron Letters*, vol. 35, No. 31, pp. 5543–5546, (1994).

*Primary Examiner*—Ba K. Trinh
*Attorney, Agent, or Firm*—Timothy J. Martin; Michael R. Henson; Mark H. Weygandt

[57] ABSTRACT

A method of acylating C-2' O-protected-10-hydroxy taxol selectively at the C-10 hydroxyl position over the C-7 hydroxy position thereof to produce C-2' O-protected taxol is accomplished first by dissolving C-2' O-protected-10-hydroxy taxol in an acceptable ether solvent therefor, such as tetrahydrofuran. A lithium salt, preferably lithium chloride, is added. A trialkylamine base or pyridine is next added, followed by the addition of an acylating agent, such as acetyl chloride. The resulting solution may be quenched, for example with ammonium chloride, to eliminate excess of the acylating agent. This solution may then be diluted with ethyl acetate to form an organic phase and an aqueous phase, with the organic phase being washed and thereafter reduced. Recrystallization and column chromatography may be employed to purify the C-2' O-protected taxol.

23 Claims, No Drawings

METHOD FOR SELECTIVE ACYLATION OF C-2'-O-PROTECTED-10-HYDROXY-TAXOL AT THE C-10 POSITION

FIELD OF THE INVENTION

This invention generally relates to the synthesis of paclitaxel from precursor compounds. More particularly, though, this invention concerns the selective acylation of C2'-O-protected-10-hydroxy taxols to afford C2'-O-protected taxols which may thereafter be deprotected to produce paclitaxel.

BACKGROUND OF THE INVENTION

The chemical compound referred to in the literature as taxol, and more recently "paclitaxel", has received increasing attention in the scientific and medical community due to its demonstration of anti-tumor activity. Paclitaxel has been approved for the chemotherapeutic treatment of several different varieties of tumors, and the clinical trials indicate that paclitaxel promises a broad range of potent anti-leukemic and tumor-inhibiting activity. As is known, paclitaxel is a naturally occurring taxane diterpenoid having the formula and numbering system as follows:

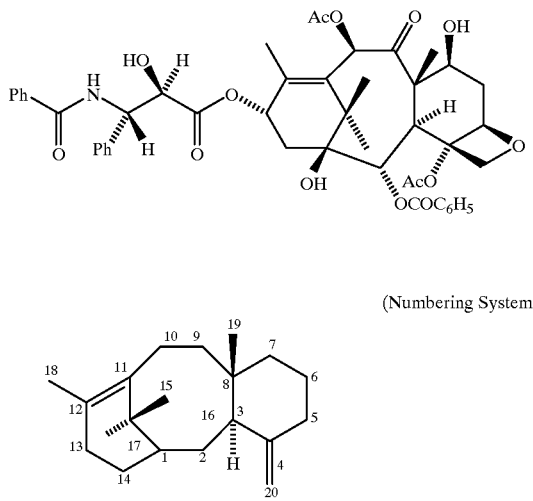

(Numbering System)

While the paclitaxel molecule is found in several species of yew (genus Taxus, family Taxaceae), the concentration of this compound is very low. Moreover, these evergreens are slow-growing. Thus, a danger exists that the increasing use of paclitaxel as an effective anti-cancer agent will deplete natural resources int he form of the yew trees. Indeed, while the bark of the yew trees typically exhibit the highest concentration of paclitaxel, the production of 1 kilogram of paclitaxel requires approximately 16,000 pounds of bark. Thus, the long term prospects for the availability of paclitaxel through isolation is discouraging.

The paclitaxel compound, of course, is built upon the baccatin III backbone, and there are a variety of other taxane compounds, such as baccatin III, cephalomannine, 10-deacetylbaccatin III, etc., some which are more readily extracted in higher yields from the yew trees. Indeed, a relatively high concentration of 10-deacetylbaccatin III can be extracted from the leaves of the yew as a renewable resource. Typically, however, these other taxane compounds present in the yew tree do not exhibit the degree of anti-tumor activity shown by the paclitaxel compound.

Since the paclitaxel compound appears so promising as a chemotherapeutic agent, organic chemists have spent substantial time and resources in attempting to synthesize the paclitaxel molecule. A more promising route the creation of significant quantities of the paclitaxel compound has been proposed by the semi-synthesis of paclitaxel by the attachment of the A-ring side chain to the C13 position of the naturally occurring baccatin III backbone derived from the various taxanes present in the yew. See, Denis et al, a "Highly Efficient, Practical Approach to Natural Taxol". *Journal of the American Chemical Society*, page 5917 (1988). In this article, the partial synthesis of paclitaxel from 10-deacetylbaccatin III is described.

The most straightforward implementation of partial synthesis of paclitaxel requires convenient access to chiral, non-racemic side chain and derivatives, an abundant natural source of baccatin III or closely related diterpenoid substances, and an effective means of joining the two. Of particular interest then is the condensation of baccatin III of 10-deacetylbaccatin III with the paclitaxel A-ring side chain. However, the esterification of these two units if difficult because of the hindered C13 hydroxyl of baccatin III located within the concave region of the hemispherical taxane skeleton. For example, Greene and Gueritte-Voegelein reported only a 50% conversion after 100 hours in one partial synthesis of paclitaxel. *J. Am. Chem. Soc.*, 1988, 110,5917.

In U.S. Pat. No. 4,929,011 issued May 8, 1990 to Denis et al entitled "Process for Preparing Taxol", the semi-synthesis of paclitaxel from the condensation of a (2R,3S) side chain acid of the general formula:

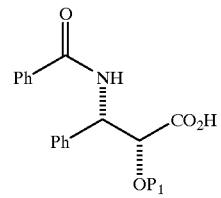

wherein $P_1$ is hydroxy protecting group with a taxane derivative of the general formula of:

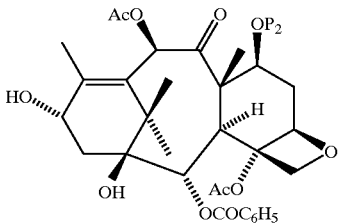

wherein $P_2$ is hydroxy protecting group is described wherein the condensation product is subsequently processed to remove the $P_1$ and $P_2$ protecting groups. In Denis et al, the (2R,3S) 3-phenylisoserine derivative, with the exception of the $P_1$ protecting group, is the A-ring side chain for the paclitaxel molecule. The $P_2$ protecting group on the baccatin III backbone is protected by, for example, a trimethylsilyl or a trialkylsilyl radical.

An alternative semi-synthesis of paclitaxel is described in co-pending U.S. patent application Ser. No. 08/357,507 to Swindell et al. This application discloses semi-synthesis of paclitaxel from a baccatin III backbone by the condensation with a side chain having the general formula:

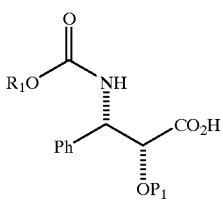

wherein $R_1$ is alkyl, olefinic or aromatic or $PhCH_2$ and $P_1$ is a hydroxyl protecting group.

The side chain in Swindell et al is distinct from the side chain attachment used in Denis et al, above in that the nitrogen is protected as a carbamate. Preferably, the A-ring side chain is benzyloxycarbonyl (CBZ) protected. After esterification, the CBZ protecting group is removed and replaced by PhCO to lead to paclitaxel. This process generated higher yields than that described in Denis et al. In Swindell et al, Ser. No. 08/357,507, the preferred masking groups were selected to be trichloroethoxymethyl or trichloroethoxycarbonyl. Benzyloxymethyl (BOM) was, however, disclosed as a possible side chain, but, according to the processes described therein, the BOM protecting group could not be removed from the more encumbered C-2' hydroxyl in the attached 3-phenylisoserine side chain. The use of the BOM protected side chain was not extensively investigated, for the reason. U.S. Pat. No. 5,675,025 issued Oct. 7, 1997 to Sisti et al describes methodology for successfully using the C2'OBOM side chain in paclitaxel synthesis. Most importantly is the disclosure of a method to remove the C2'OBOM group in C2'-OBOM taxol to produce paclitaxel.

U.S. Pat. No. 4,924,012, issued May 8, 1990 to Colin et al discloses a process for preparing derivatives of baccatin III and of 10-deacetylbaccatin III, by condensation of an acid with a derivative of a baccatin III or of 10-deacetylbaccatin III, with the subsequent removal of protecting groups by hydrogen. Several syntheses of TAXOTERE® (Registered to Rhone-Poulenc Sante) and related compounds have been reported in the Journal of Organic Chemistry: 1986, 51, 46; 1990, 55, 1957; 1991, 56, 1681; 1991, 56, 6939; 1992, 57, 4320; 1992, 57, 6387; and 993, 58, 255; also, U.S. Pat. No. 5,015,744 issued May 14, 1991 to Holton describes such a synthesis. U.S. Pat. No. 5,688,977 issued Nov. 18, 1997 to Sisti et al describes an efficient methodology to synthesize docetaxel (TAXOTERE®).

Despite the advance made in the semi-synthesis of the paclitaxel molecule in the above described processes, there remains a need for more efficient protocols for the synthesis of paclitaxel in order to increase efficiencies in yields and production rates. There remains such a need for semi-synthesis that may be implemented into commercial processes. There is a further need for efficient protocols for the synthesis of paclitaxel analogs, intermediates and various A-ring side chain structures.

SUMMARY OF THE INVENTION

It is an object of the present invention to provide a new, useful, efficient protocol for the selective C10 acylation of C2'-O-protected-10-hydroxy taxol to provide C2'-O-protected taxol which may then be converted into paclitaxel.

It is still a further object of the present invention to provide a new and useful protocol for the semi-synthesis of paclitaxel in an effort to provide a high yield of paclitaxel in a cost efficient manner.

Yet another object of the present invention is to provide a method for the production of paclitaxel which can be scaled to commercial implementation.

The production process is directed at a method of acylating C2'-O-protected-10-hydroxy-taxol selectively at the C10 hydroxyl position over the C7 hydroxyl position.

According to the general method, C2'-O-protected-10-hydroxy taxol of the formula:

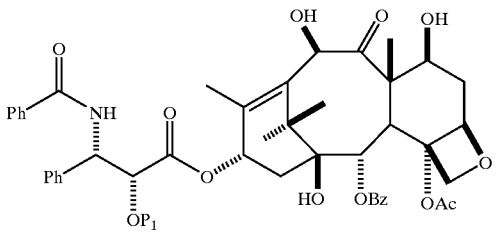

is dissolved in an acceptable ether solvent to form a first solution. Next, a solution containing a lithium salt, preferably lithium chloride in tetrahydrofuran, is mixed into the first solution to form a second solution. Next, a base selected from a group consisting of trialkyl amine bases and pyridine is added to the second solution to form a third solution. Next, an acylating agent, preferably acetyl chloride, is combined with the third solution to form a fourth solution containing C2'-O-protected taxol.

In this method, it is preferred that approximately five equivalents of the lithium salt in solution is added to the first solution to form the second solution; however, the lithium salt may be in a range of approximately one to five equivalents thereof. It is also preferred that approximately five equivalents of the base be added to the second solution to form the third solution although between two and ten equivalents of the base may be added. This base is preferably triethyl amine.

The third solution may be added to a solution containing between two and ten equivalents of the acylating agent to from the fourth solution. Preferably, approximately five equivalents of the acylating agent are dissolved in tetrahydrofuran into which the third solution is added to form the fourth solution. This fourth solution is then stirred for an interval of one-half to twenty-four hours, although higher yields are present at the longer duration.

The method according to the present invention can be continued by quenching the fourth solution with a suitable quenching compound that is effective to eliminate excess of the acylating agent therefrom thereby to produce a fifth solution. Thereafter, the organic phase may be washed with 1 Normal HCl and brine thereafter reduced to a first residue. This first residue may be purified, such as by column chromatography, recrystallization and the like to afford C2'-O-protected taxol.

The ether solvent for the preferred method is selected from a group consisting of tetrahydrofuran and polyethers. It is preferred that the ether solvent be anhydrous. The preferred acylating agent is acetyl chloride and the preferred quenching compound is ammonium chloride solution. The steps of the method are performed preferably at a temperature between −10° C. and 30° C., although the preferred temperature is approximately 25° C.

These and other objects of the present invention will become more readily appreciated and understood when the following detailed description of the exemplary embodiment is considered.

DETAILED DESCRIPTION OF THE EXEMPLARY EMBODIMENTS

The present disclosure is broadly directed to a chemical process for the efficient production of paclitaxel. More specifically, the present disclosure is directed at methodology to convert C2'-O-protected-10-hydroxy-taxol to C2'-O-protected taxol which are useful intermediates in paclitaxel semi-synthesis as disclosed in U.S. Pat. No. 5,675,025. The method is described for C2'-O-BOM protected taxol as the exemplary embodiment. However, other protecting groups at C2' should be possible for the starting compound.

The general process described herein involves the production of the C7, C10 di-CBZ 10-deacetylbaccatin III backbone, the production of the suitable protected 3-phenylisoserine acid having a C2' protecting group, the condensation of the two compounds, the subsequent deprotection at C7 and C10 as well as at the C3' nitrogen site as described in U.S. Pat. No. 5,688,977. Acylation at the C3' nitrogen site is performed to add the benzoyl group, selective acylation at the C10 hydroxyl site over the C7 hydroxyl site to add the acetyl group followed by further deprotection to yield paclitaxel.

A. Production of C7, C10 dicarbobenzyloxy 10-deacetylbaccatin III

C7, C10 di-CBZ 10-deacetylbaccatin III is produced by the following reaction:

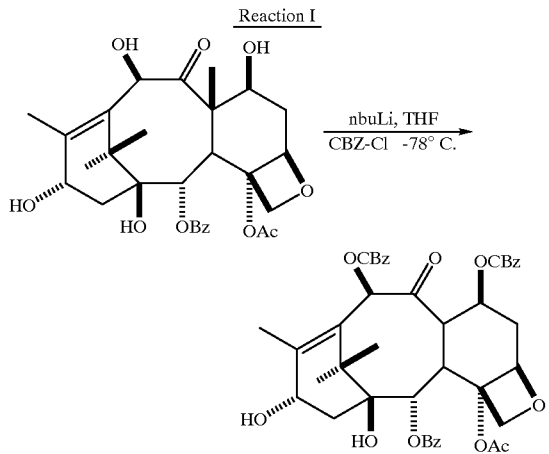

Here, 10-deacetylbaccatin III is dissolved in anhydrous THF (tetrahydrofuran) and is cooled under a nitrogen atmosphere to a temperature of less than −20° C. but preferably −78° C. n-butyl lithium (1.6M in hexane) is added dropwise and the solution is stirred at the reduced temperature for approximately five minutes. At least 1.5 equivalents of n-butyl lithium are needed to get significant product yield, however two equivalents are preferable. Benzyl chloroformate is then added dropwise (again, at least 1.5 equivalents of the benzyl chloroformate are needed for significant yield, but two equivalents are preferred) and the mixture is stirred over a period of one hour during which time it is allowed to warm to a temperature of no more than 0° C. The mixture is then quenched with cold saturated ammonium chloride to eliminate any excess n-butyl lithium and acetyl chloride, and the mixture is reduced under vacuum. the residue is taken up in ethyl acetate and washed once with water and then with brine to remove unwanted salts. The organic layer may then be dried and reduced under vacuum, and the residue recrystallized or column chromatagraphed with ethyl acetate/hexane to yield C7, C10 di-CBZ 10-deacetylbaccatin III as a white solid in greater than 80% overall yield.

B. Production of the 3-Phenylisoserine Side Chain

The production of the (2R,3S)N-CBZ C2'O-protected 3-phenylisoserine ethyl ester side chain, where the C2' hydroxy group is protected by a hydrogenatable benzyl-type protecting group can be accomplished from the starting compound (2R,3S) 3-phenylisoserine ethyl ester according to the following two reactions. The first reaction is:

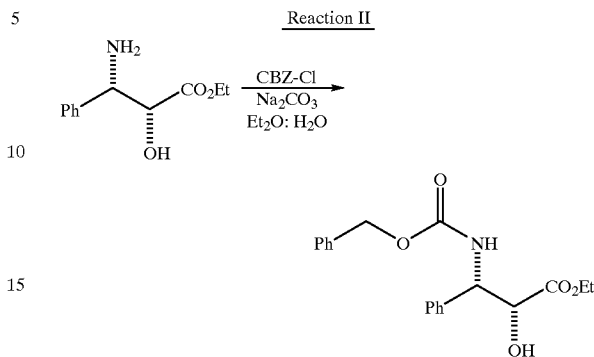

Here, (2R,3S) 3-phenylisoserine ethyl ester was alternatively dissolved in either equal parts diethyl ether:water or equal parts methyl t-butyl ether:water and the solution was cooled to 0° C. The sodium carbonate was then added to the solution and the benzylchloroformate was added dropwise over an interval of about five minutes and the resulting mixture stirred at 0° C. for approximately one hour. After the one hour stirring, the solution was then poured into water and extracted with methylene chloride or ethyl acetate, as desired. The organic layer is separate, dried and reduced under vacuum to residue. The residue was then recrystallized from ethyl acetate:hexane to result in N-CBZ 3-phenylisoserine ethyl ester.

This intermediate was next protected by the hydrogenatable benzyl-type protecting group in several ways. For example, one route to the desired hydrogentable benzyl-type protected side chain is as follows:

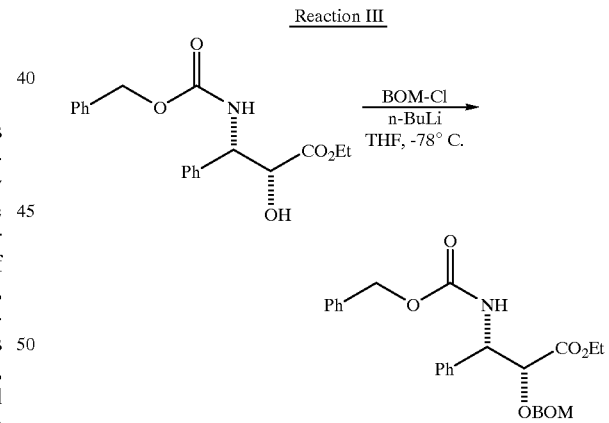

Here, the hydrogenatable benzyl-type protecting group is benzyloxymethyl (BOM). To prepare this compound, the N-CBZ 3-phenylisoserine ethyl ester is dissolved in anhydrous THF under a nitrogen atmosphere and cooled to a reduced temperature such as −20° C. or −78° C., for example, in a dry ice/acetone bath followed by the dropwise addition of an alkyllithium agent such as n-butyl lithium although it is desirable that the alkyllithium agent be a straight chain alkyl. In any event, the reaction is best done at a temperature no greater than 0° C. The resulting mixture is stirred for about ten minutes. Benzyloxymethyl chloride (BOM-Cl) is then added dropwise over an interval of about five minutes and the mixture stirred for approximately two to five hours at the reduced temperature. Thereafter, the solution is warmed to 0° C. and quenched with water to eliminate excess n-butyl lithium. The resulting mixture is reduced under vacuum to residue, and this residue is thereafter taken up in ethyl acetate and washed with water and brine to remove unwanted salts. The organic layer may then be dried and reduced under vacuum and the residue recrystallized from ethyl acetate:hexane or chromatographed with ethyl acetate:hexane to give the N-CBZ C2'-BOM 3-phenylisoserine ethyl ester.

Another route to production of N-CBZ C2'-OBOM 3-phenylisoserine ethyl ester is accomplished by dissolving the compound N-CBZ (2R,3S)-3-phenylisoserine ethyl ester in anhydrous methylene chloride. Thereafter, a tertiary amine base such as diisopropylethylamine is added along with BOM-Cl and the mix is refluxed for twenty-four hours. While this reaction route will produce N-CBZ 2'-BOM-3-phenylisoserine ethyl ester, the reaction proceeds much more slowly than the route discussed above. However, it may be preferred because of higher yield. Here, the compound is not purified, but rather is carried on to subsequent processing steps in crude form.

In either instance, the resulting N-CBZ C2'-OBOM (2R, 3S)-3-phenylisoserine ethyl ester, either in the purified form of the first route or in the crude form from the second route, may simply be converted to the corresponding acid by the reaction:

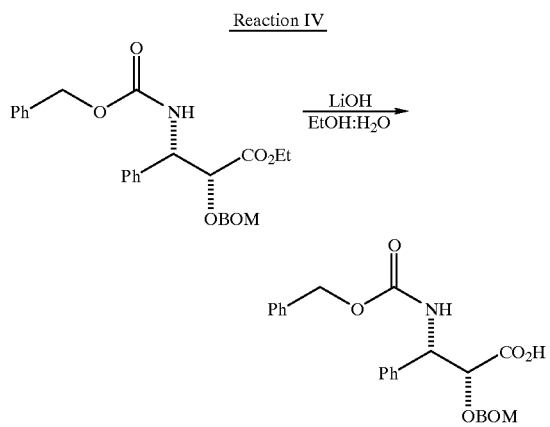

Here, the protected ethyl ester is dissolved in ethanol/water (ratio 8:1). Lithium hydroxide (or other suitable alkali hydroxide) is added to the solution and the resulting mixture stirred for approximately three hours in order to saponify the compound. The mixture is then acidified (1N hydrochloric acid) and extracted with ethyl acetate. The resulting organic layer is separated, dried and reduced under vacuum. the residue acid is then isolated for use without further purification. This produces the desired N-CBZ C2'-OBOM (2R, 3S)-3-phenylisoserine.

Where N-CBZ C2'-OBOM 3-phenylisoserine ethyl ester is carried forward in the crude form and is converted into N-CBZ C2'-OBOM (2R,3S)-3-phenylisoserine, it is necessary for further purification of the end product. This purification is accomplished by dissolving the product in toluene followed by the dropwise addition of one equivalent of dicyclohexylamine and the resulting solution is stirred for one-half hour. This mixture is then concentrated in vacuo, and the resulting residue is recrystallized from ethyl acetate:hexane to give the dicyclohexylamine salt of the N-CBZ C2'-OBOM (2R,3S)-3-phenylisoserine may then be liberated by dissolving this dicyclohexylamine salt in methylene chloride or another halogenated solvent followed by washing the methylene chloride with several portions of 1N HCl. The organic layer is then washed with several portions of water to remove dicyclohexylamine hydrochloride. Next, it is washed with one portion of saturated brine and reduced vacuo to give the desired acid.

Benzyl itself is another example of a hydrogenatable benzyl-type protecting group that may be used instead of BOM. N-CBZ 2'-benzyl 3-phenylisoserine ethyl ester was produced as above with the substitution of benzyl bromide for BOM-Cl according to the reaction:

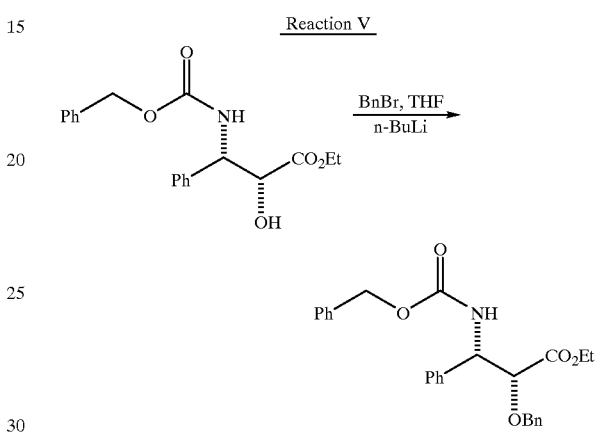

Here, the CBZ protected (2R,3S)-3-phenylisoserine ethyl ester is dissolved in anhydrous THF under a nitrogen atmosphere and cooled to a reduced temperature such as −20° C. or −78° C. for example in a dry ice/acetone bath followed by the dropwise addition of an alkyllithium agent such as n-butyl lithium, although it is desirable that the alkyllithium agent be a straight chain alkyl. The resulting mixture is stirred for about ten minutes. Benzyl bromide (BnBr) is then added dropwise over an interval of about five minutes and the mixture is stirred for approximately two to five hours at the reduced temperature. Thereafter, the solution is warmed to 0° C. and quenched with water to destroy excess n-butyl lithium. The resulting mixture is reduced under vacuum to residue, and this residue is thereafter taken up in ethyl acetate and washed with water to remove any lithium bromide salt; it is then further washed with brine. The organic layer may then be dried and reduced under vacuum and the residue recrystallized from ethyl acetate;hexane or chromatographed with ethyl acetate;hexane to give N-CBZ 2'-benzyl 3-phenylisoserine ethyl ester.

Alternatively, the N-CBZ 2'-benzyl 3-phenylisoserine ethyl ester may be obtained according to the reaction:

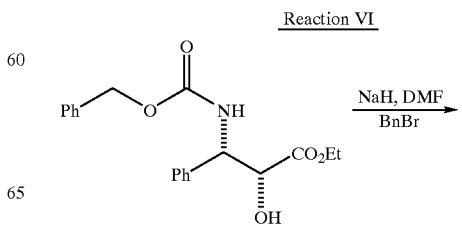

9

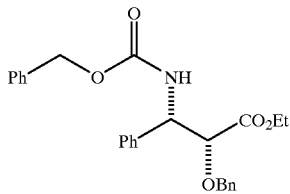

Here, to a stirred solution of NaH in anhydrous DMF under nitrogen is added N-CBZ-3-phenylisoserine ethyl ester dissolved in DMF over five minutes. The mixture is then stirred at 0° C. for one half hour. Then benzyl bromide (1.1 equivalents) is added dropwise over five minutes and the reaction is stirred for two hours. The mixture is then quenched with water to destroy excess sodium hydride. Thereafter, either diethyl ether or methyl t-butyl ether is added. The organic layer is then washed with four portions of water to remove DMF and sodium bromide. Next, it is washed with brine and then dried and reduced under vacuum to produce N-CBZ C2'-benzyl 3-phenylisoserine ethyl ester may then be readily converted into N-CBZ C2'-benzyl 3-phenylisoserine by the process of Reaction IV above with the understanding that, in this case, benzyl is the C2' protecting group instead of benzyloxymethyl (BOM).

C. Esterification of the Protected Baccatin III with the Side Chain

Esterification of the C7, C10 di-CBZ 10-deacetylbaccatin III with the N-CBZ C2'-protected 3-phenylisoserine side chain (where the C2' hydroxyl is protected by an hydrogenatable benzyl-type group) is accomplished as follows. The preferred hydrogenatable benzyl group shown below is BOM (benzyloxymethyl).

Reaction VII

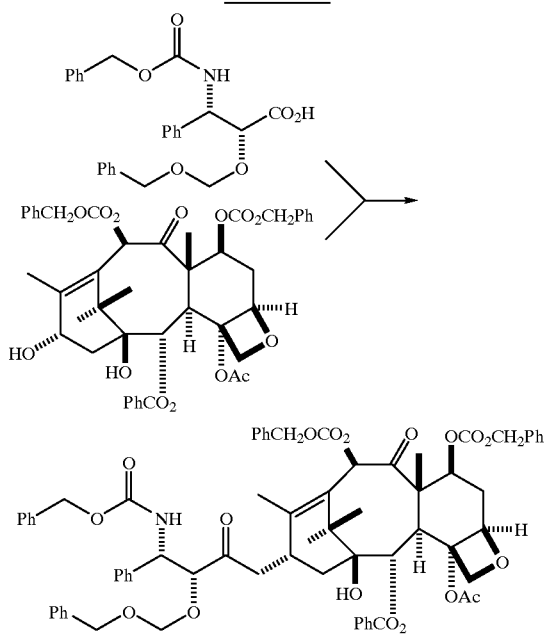

Here, the C7, C10 di-CBZ 10-deacetylbaccatin III (one equivalent) and the acid side chain (six equivalents) are dissolved in toluene. To this mixture, 4-dimethylamino pyridine (DMAP) (one equivalent) and dicyclohexylcarboiimide (six equivalents) are added, and the resulting mixture heated at about 60° C. to 80° C. for one to five hours. It

10 should also be noted, however, that other dialkylcarbodiimides may be substituted for the dicyclohexylcarbodiimide with one example being diisopropylcarbodiimide.

The solution is then allowed to cool to room temperature, and next an equal volume of diethyl ether or ethyl acetate is added. The resulting solution is cooled to 0° C. with stirring and held at this temperature for twenty-four hours. This step crystallizes most of the urea impurity. After the twenty-four hour interval elapses, the solution is filtered and the residue rinsed with either ethyl ether or methyl t-butyl ether or ethyl acetate. The combined organics are then washed with hydrochloric acid (5%), water and finally brine. The organic phase is separated, dried and reduced under vacuum. The resulting residue is then dissolved in ethyl acetate:hexane and eluted over a silica gel plug. The eluent is then reduced under vacuum to a residue. The residue is then recrystallized from diethyl ether to result in the desired coupled product, namely, C3' NCBZ C2'-OBOM-C7, C10-di-CBZ 10-deacetylbaccatin III of the formula:

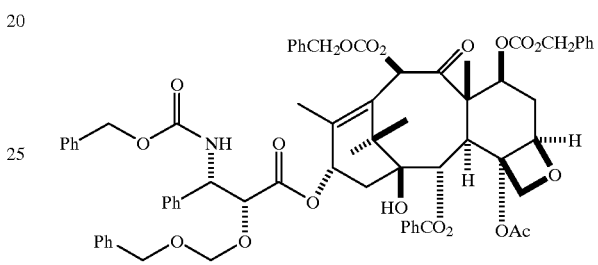

D. Deprotection and Treatment with Benzoyl Chloride

The following reaction removes the CBZ protecting groups at C7 and C10 and the C3' nitrogen side chain site to produce the desired amine. (Again for clarity, BOM is used here as an example of a C2' hydrogenatable benzyl-type protecting group):

Reaction VIII

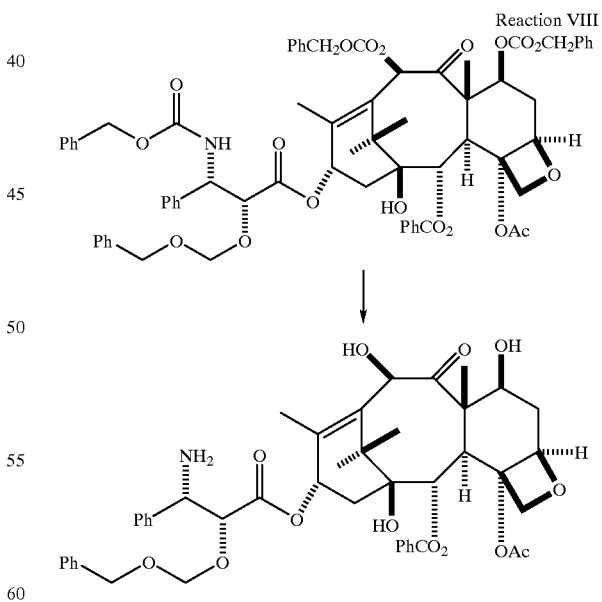

The coupled product is dissolved in isopropanol/ethyl acetate to which Pearlman's catalyst is added. The resulting mixture is hydrogenated at 40 psi of hydrogen for at least twenty-four hours. This results in the amine shown in Reaction VIII. Alternatively, the coupled product may be dissolved in isopropanol/ethyl acetate and hydrogenated at 1 atm of hydrogen in the presence of Pearlman's Catalyst and one equivalent of trifuroacetic acid. This method produces the TFA salt of the amine shown by the formula:

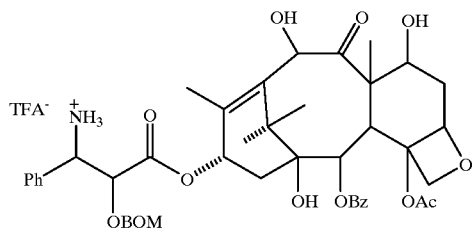

In either case, the mixture is filtered through diatomaceous earth and reduced under vacuum to residue to result in the amine or its TFA salt which is used without further purification.

Next, the amine or the amine salt is acylated at the C3' nitrogen according to the reaction:

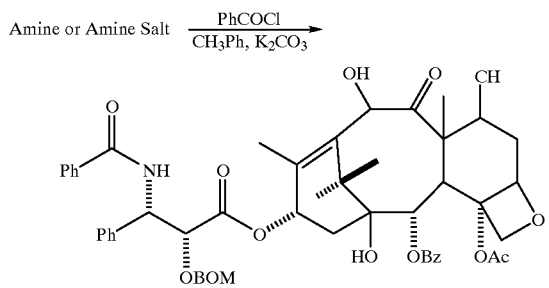

Here, the amine or, alternatively, the amine salt, is taken up in anhydrous toluene and potassium carbonate added, followed by the addition of benzoyl chloride. The mixture is then stirred for at least thirty minutes, diluted with ethyl acetate, washed with water and brine. The resulting organic phase is then separated, dried over magnesium sulfate and reduced under vacuum to get crude C2'-OBOM 10-hydroxy taxol. It is necessary at this stage of processing to purify the crude C2'-OBOM-10-hydroxy taxol. This can be accomplished by column chromatography and/or recrystallization from ethyl acetate:hexane. Preferably both column chromatography with ethyl acetate:hexane to produce an eluent that is reduced in vacuo to form a residue followed by recrystallization of the residue from ethyl acetate:hexane is employed to give C2'-OBOM-10-hydroxy taxol in substantially pure form. Alternatively, the amine or the amine salt may be taken up in anhydrous tetrahydrofuran and at least one equivalent of a tertiary amine base such as diisopropylethyl amine added followed by benzoyl chloride.

E. Selective C10 Acylation With Triethylamine Lithium Chloride and Acetyl Chloride and Deprotection to Form Paclitaxel The following reaction selectively acylates the C10 hydroxy group in the presence of the C7 hydroxy group. While any protecting group at C2' should behave similarly, for clarity, BOM is used here as an example of a C2' hydrogenatable benzyl-type protecting group:

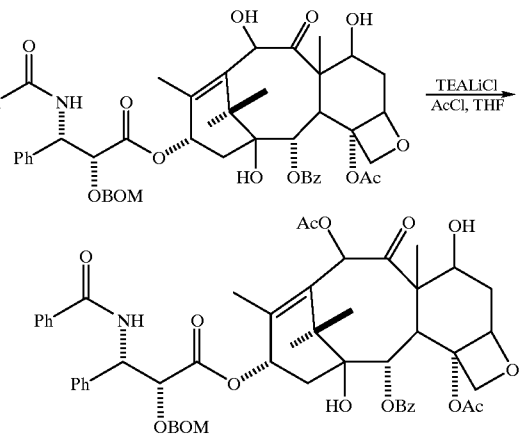

Here, C2'-OBOM-10-hydroxy taxol is taken up in an acceptable ether solvent preferably anhydrous tetrahydrofuran at a temperature of between −10° and 30° C. but preferably 25° C. to form a first solution. Next, a solution of one to five equivalents of lithium salt preferably lithium chloride in an acceptable ether solvent preferably anhydrous tetrahydrofuran is mixed into the first solution to from a second solution. Next, two to ten equivalents but preferably five equivalents of trialkylamine base or pyridine but preferably triethylamine are added to the second solution to form a third solution. Next, two to ten equivalents but preferably five equivalents of acetyl chloride are added to the third solution to form a fourth solution. The fourth solution is then stirred for at least one-half hour but preferably twenty-four hours, quenched with a suitable quenching compound preferably ammonium chloride solution, diluted with ethyl acetate forming an aqueous phase organic phase, the aqueous phase is discarded at the organic phase, washed with one normal HCl, brine, reduced to a first residue and purified by column chromatography with ethyl acetate:heptane to afford C2'-OBOM-taxol in substantially pure form.

As previously shown in U.S. Pat. No. 5,675,025, the benzyloxymethyl protecting group is removed as follows:

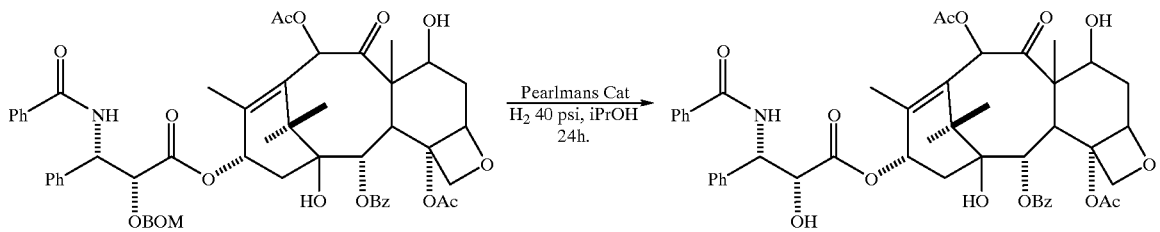

Here, the purified C2'-OBOM taxol is dissolved in isopropanol and Pearlman's catalyst is added. The mixture is then hydrogenated at either 1 Atm of hydrogen with catalytic trifluroacetic acid added or at 40 psi hydrogen without trifluroacetic acid added for at least twenty-four hours. In either case, the mixture is then filtered through diatomaceous earth and reduced under vacuum to get crude paclitaxel.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A method of acylating C2'O-protected-10-hydroxy taxol selectively at the C10 hydroxyl position over the C7 hydroxy position thereof, comprising the steps of:
   (a) dissolving a selected quantity of a C2'-O-protected -10-hydroxy taxol in an acceptable ether solvent therefor to form a first solution;
   (b) mixing a solution containing a lithium salt into the first solution to form a second solution;
   (c) adding a base selected from a group consisting of trialkyl amine bases and pyridine to the second solution thereby to form a third solution; and
   (d) combining the third solution with an acylating agent to from a fourth solution such that C2'-O-protected taxol is formed in the fourth solution.

2. A method according to claim 1 wherein approximately five equivalents of lithium salt in solution is added to the first solution to form the second solution.

3. A method according to claim 2 wherein the lithium salt is dissolved in tetrahydrofuran.

4. A method according to claim 1 wherein approximately five equivalents of the base is added to the second solution to form the third solution.

5. A method according to claim 1 wherein the third solution is added to a solution containing the acylating agent to form the fourth solution.

6. A method according to claim 1 including the step of stirring the fourth solution for a period of at least one-half hour.

7. A method according to claim 1 including the step of quenching the fourth solution with a suitable quenching compound that is effective to eliminate excess of said acylating agent therefrom to produce a fifth solution.

8. A method according to claim 1 wherein said quenching compound is ammonium chloride solution.

9. A method according to claim 7 including the step of diluting said fifth solution with ethylacetate to from an organic phase and an aqueous phase.

10. A method according to claim 9 including the step of washing the organic phase with 1 Normal HCl and brine and thereafter reducing the organic phase to a first residue.

11. A method according to claim 10 including the step of purifying the first residue to afford C2'-O-protected taxol.

12. A method according to claim 1 wherein said ether solvent is selected from a group consisting of tetrahydrofuran and polyethers.

13. A method according to claim 1 wherein said ether solvent is anhydrous.

14. A method according to claim 1 wherein said acylating agent is acetyl chloride.

15. A method according to claim 1 wherein steps (a)–(d) are performed at a temperature of between −10° C. and 30° C.

16. A method according to claim 1 wherein one to five equivalents of a lithium salt, dissolved in tetrahydrofuran is mixed into the first solution to form the second solution at a first temperature.

17. A method according to claim 1 wherein said lithium salt is selected from a group consisting of lithium chloride and lithium iodide.

18. A method according to claim 1 wherein two to ten equivalents of said base are mixed into the second solution to form a third solution.

19. A method according to claim 18 wherein about five equivalents of said base are mixed into the second solution to form a third solution.

20. A method according to claim 19 wherein said base is triethyl amine.

21. A method according to claim 1 wherein the third solution is added to a solution of two to ten equivalents of acylating agent to form the fourth solution.

22. A method according to claim 21 wherein about five equivalents of the acylating agent is dissolved in THF into which the third solution is added to form a fourth solution.

23. A method according to claim 1 wherein said fourth solution is stirred for about twenty-four hours.

* * * * *